(12) United States Patent
McBride, Jr. et al.

(10) Patent No.: US 10,959,716 B2
(45) Date of Patent: Mar. 30, 2021

(54) SURGICAL RETRACTOR SYSTEM AND METHOD

(71) Applicant: Warsaw Orthopedic, Inc., Warsaw, IN (US)

(72) Inventors: Larry Thomas McBride, Jr., Memphis, TN (US); Christel Italiaie, Memphis, TN (US); Madeline G. Wilson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/395,550

(22) Filed: Apr. 26, 2019

(65) Prior Publication Data
US 2020/0253595 A1    Aug. 13, 2020

Related U.S. Application Data

(63) Continuation-in-part of application No. 16/272,640, filed on Feb. 11, 2019.

(51) Int. Cl.
*A61B 17/02* (2006.01)
*A61B 34/30* (2016.01)
*A61B 90/50* (2016.01)
*A61B 17/00* (2006.01)

(52) U.S. Cl.
CPC .......... *A61B 17/0206* (2013.01); *A61B 34/30* (2016.02); *A61B 90/50* (2016.02); *A61B 17/0218* (2013.01); *A61B 2017/00477* (2013.01)

(58) Field of Classification Search
CPC . A61B 17/0206; A61B 17/0218; A61B 34/30; A61B 90/50; A61B 2017/00477
USPC .................................................. 600/201–249
See application file for complete search history.

(56) References Cited

U.S. PATENT DOCUMENTS

| | | | | |
|---|---|---|---|---|
| 5,512,038 | A * | 4/1996 | O'Neal .............. | A61B 17/0206 600/210 |
| 9,675,332 | B2 * | 6/2017 | Beck .................. | A61B 17/0206 600/210 |
| 9,872,676 | B2 * | 1/2018 | Weisshaupt ........ | A61B 17/0206 600/210 |
| 10,383,613 | B2 * | 8/2019 | Daavettila .......... | A61B 17/0206 600/210 |
| 2007/0161865 | A1 * | 7/2007 | Fakhrai .............. | A61B 17/0206 600/231 |
| 2008/0188718 | A1 * | 8/2008 | Spitler ............... | A61B 17/0206 600/213 |
| 2009/0203969 | A1 * | 8/2009 | Cohen ................ | A61B 17/0206 600/245 |
| 2010/0113885 | A1 * | 5/2010 | McBride ............ | A61B 17/0293 600/224 |

(Continued)

*Primary Examiner* — Jessica Weiss
(74) *Attorney, Agent, or Firm* — Sorell, Lenna & Schmidt, LLP

(57) ABSTRACT

A surgical retractor includes a part defining a longitudinal axis. A first radiolucent blade is connected with the part. A second radiolucent blade is connected with the part. The blades are independently translatable relative to the part. At least one of the blades includes spaced apart arms that are connected via a member. The member and the arms are relatively disposed in a configuration to guide at least one surgical instrument in a selected orientation relative to a surgical site. Surgical systems, instruments, constructs, implants and methods are disclosed.

19 Claims, 12 Drawing Sheets

(56) References Cited

U.S. PATENT DOCUMENTS

| | | | |
|---|---|---|---|
| 2010/0222644 A1* | 9/2010 | Sebastian | A61B 17/0206 600/228 |
| 2012/0296171 A1* | 11/2012 | Lovell | A61B 17/708 600/213 |
| 2014/0135584 A1* | 5/2014 | Lee | A61N 1/0551 600/202 |
| 2016/0192922 A1* | 7/2016 | Friedrich | A61B 17/0206 600/214 |
| 2017/0311940 A1* | 11/2017 | Daavettila | A61B 17/0206 600/210 |
| 2020/0253594 A1* | 8/2020 | Wilson | A61B 17/7074 |

* cited by examiner

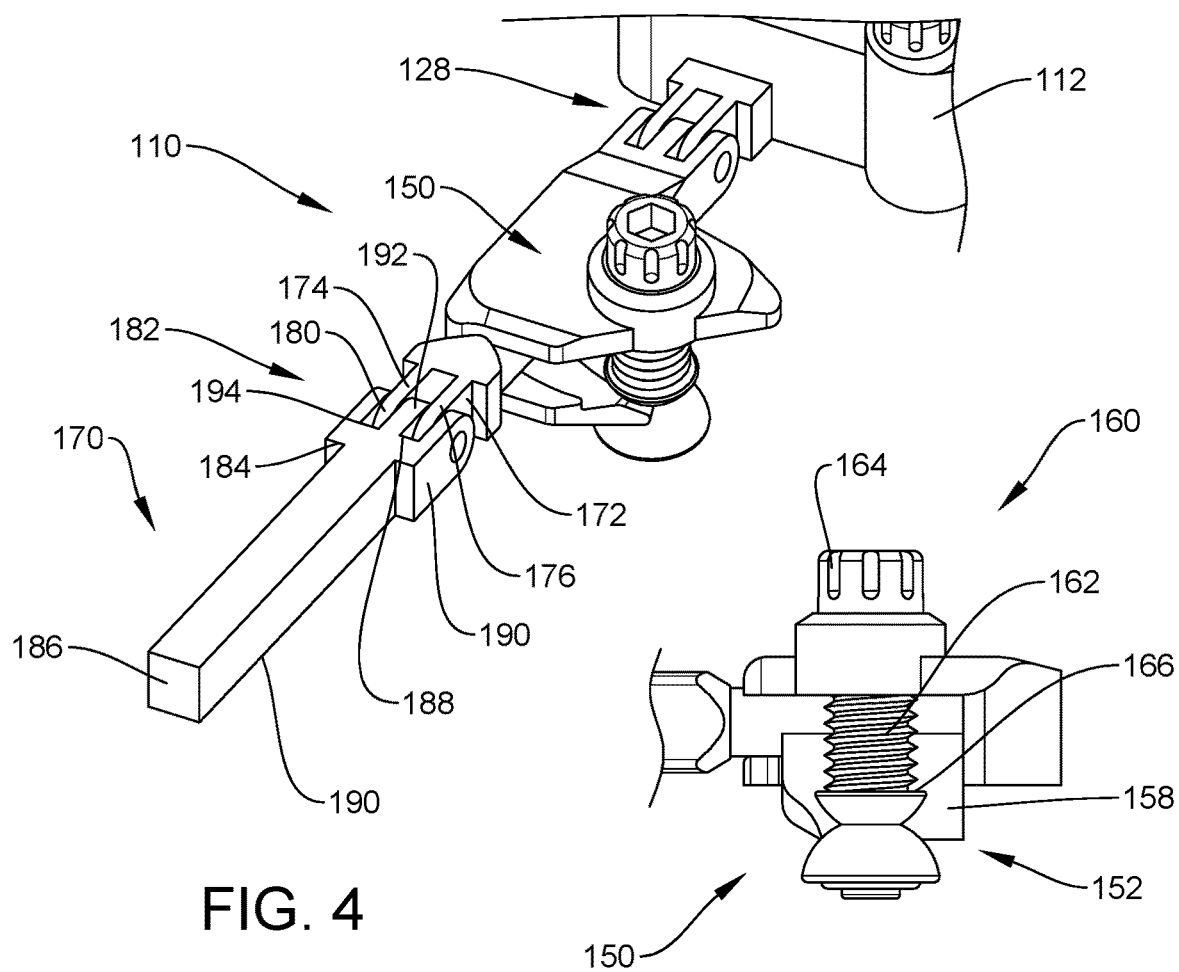
FIG. 4
FIG. 5
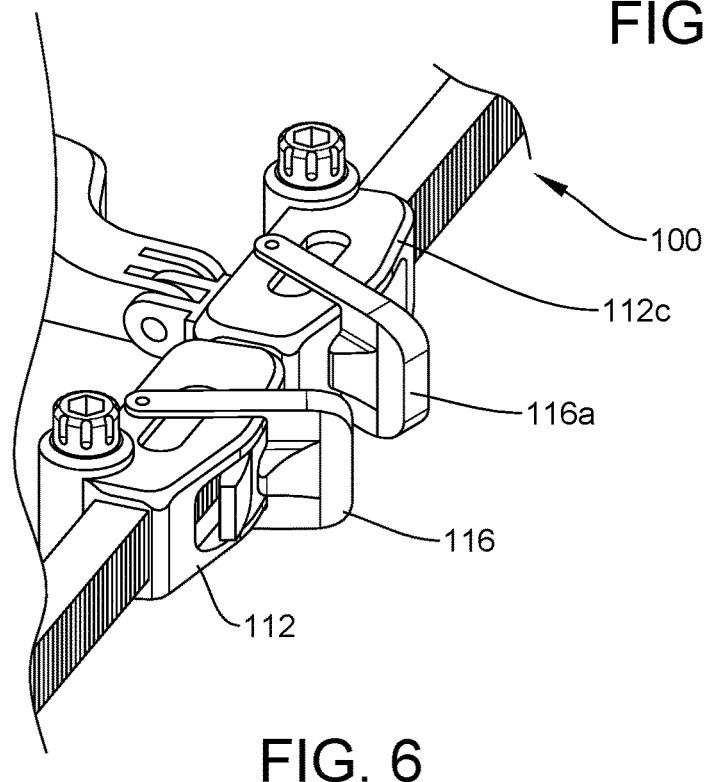
FIG. 6

SURGICAL RETRACTOR SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy, corpectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior technologies.

SUMMARY

In one embodiment, a surgical retractor is provided. The surgical retractor includes a part defining a longitudinal axis. A first radiolucent blade is connected with the part. A second radiolucent blade is connected with the part. The blades are independently translatable relative to the part. At least one of the blades includes spaced apart arms that are connected via a member. The member and the arms are relatively disposed in a configuration to guide at least one surgical instrument in a selected orientation relative to a surgical site. In some embodiments, surgical systems, instruments, constructs, implants and methods are disclosed.

In one embodiment, the surgical retractor includes a rack defining a longitudinal axis, a first extension and a second extension. The extensions are independently movable relative to the rack. A first radiolucent blade is connected with and rotatable relative to the first extension. A second radiolucent blade is connected with and rotatable relative to the second extension. The blades are independently translatable relative to the part. Each of the blades include spaced apart arms connected via a member. The member and the arms are relatively disposed in a configuration to guide at least one surgical instrument in a selected orientation relative to a surgical site.

In one embodiment, a surgical system is provided. The surgical system includes a surgical retractor having a part defining a longitudinal axis. A first radiolucent blade and a second radiolucent blade are connected with and independently translatable relative to the part. At least one of the blades includes spaced apart arms connected via a member. The member and the arms are relatively disposed in a configuration to guide at least one surgical instrument in a selected orientation relative to a surgical site. A guide member includes an inner surface that defines a cavity configured for disposal of the at least one surgical instrument and an image guide being oriented relative to a sensor to communicate a signal representative of a position of the guide member. A tracking device includes a sensor that receives the signal and communicates with a processor to generate data for display of an image from a monitor. The image represents position of the guide member relative to tissue.

BRIEF DESCRIPTION OF THE DRAWINGS

The present disclosure will become more readily apparent from the specific description accompanied by the following drawings, in which:

FIG. 4 is a perspective break-away view of components shown in FIG. 2;

FIG. 5 is a side break-away view of the components shown in FIG. 2;

FIG. 6 is a break-away perspective view of components of one embodiment of a surgical system in accordance with the principles of the present disclosure;

DETAILED DESCRIPTION

Figure 1:
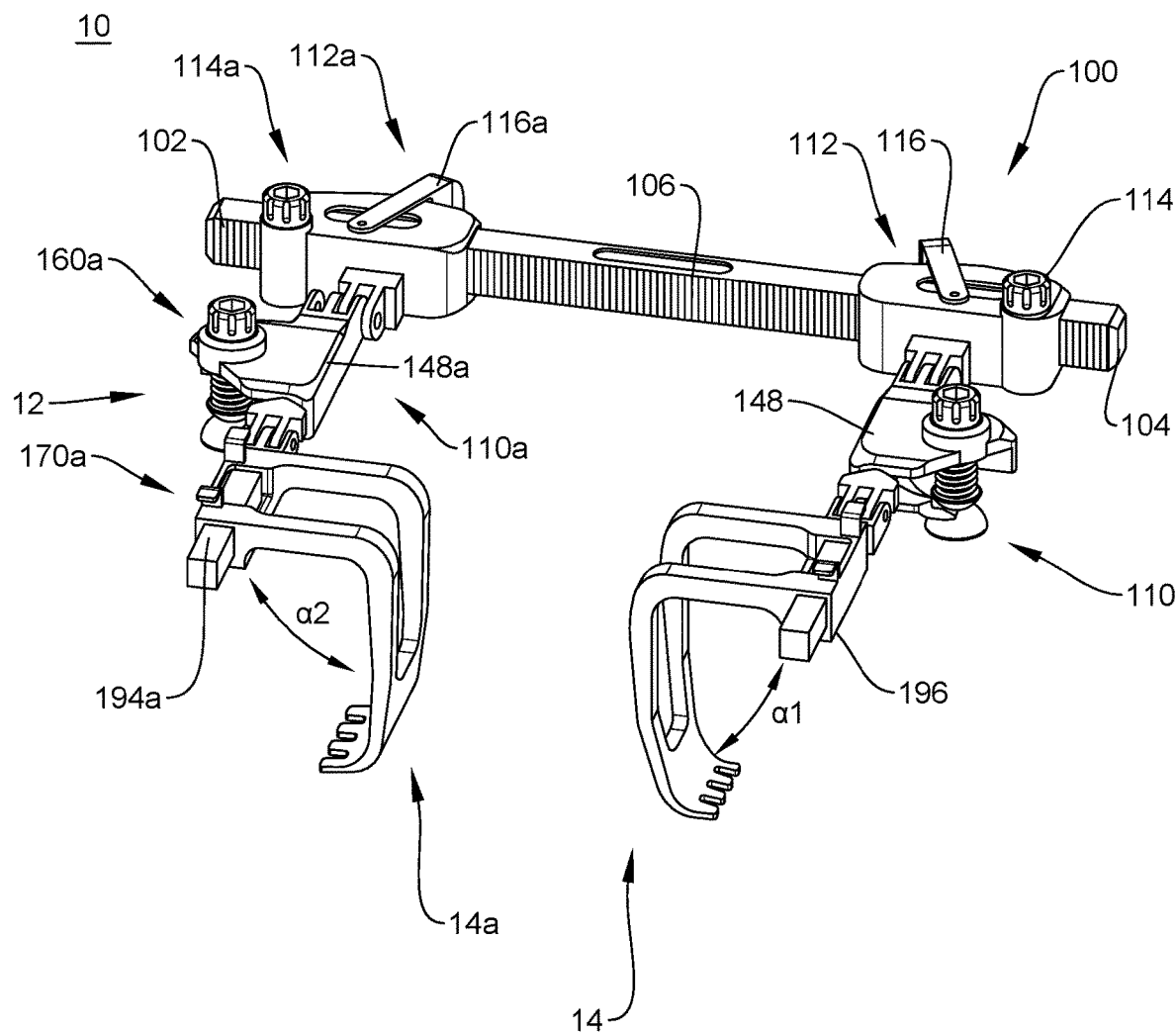
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for accessing a spine to facilitate treatment thereof and a method for treating a spine. In some embodiments, the systems and methods of the present disclosure comprise one or more retractor blades that are configured to provide selective orientation and positioning of surgical instrumentation and/or support of patient anatomy. In some embodiments, the retractor blade includes surfaces and/or openings to provide selective orientation and positioning of surgical instrumentation and/or support of patient anatomy. In some embodiments, the retractor blade includes a cutout that provides instrumentation and anatomical relief.

In some embodiments, the present surgical system comprises a surgical instrument, for example, a surgical retractor blade configured to facilitate a contralateral decompression and/or a discectomy during a midline posterior thoracolumbar approach by allowing posterior instrumentation to be angulated laterally as well as cephalad-caudally via surfaces and/or openings of the surgical retractor blade, for example, surfaces defining a cutout, while maintaining retraction of soft tissue out of a working surgical field. In some embodiments, the cutout provides for anatomical relief to facilitate an increase of insertion of the retractor into a patient body adjacent to the working surgical field without impinging on the facets or the transverse processes. In some embodiments, the cut out includes an arcuate configuration. In some embodiments, the cut out includes a square configuration.

In some embodiments, the present surgical system comprises a surgical instrument, for example, a surgical retractor having radiolucent components, such as, for example, various components made with carbon fiber. In some embodiments, the radiolucent components facilitate registration for navigation or robotic accuracy. In some embodiments, the radiolucent components facilitate registering anatomy with tissue already retracted to avoid changes and/or movement in the vertebrae after retraction of metal parts that need to be removed for registration capability.

In some embodiments, the present surgical system comprises a surgical retractor having radiolucent components to facilitate pre-operative registration for navigation assisted procedures. In some embodiments, the present surgical system comprises radiolucent blades allowing for a locating grid on imaging and the grid elements can be seen through the blades. In some embodiments, the present surgical system comprises a surgical retractor having radiolucent components, for example, components that are disposed in the incision below a skin-line.

In some embodiments, a radiolucent retraction system is provided that is configured to enable robotic and navigation registration and improve imaging. In some embodiments, a radiolucent retraction system minimizes interference of the retractor with instruments during a surgical procedure.

In some embodiments, the present surgical system comprises a surgical retractor having an optimized lighting system. In some embodiments, the present surgical system comprises a surgical retractor configured for stability when in a fully opened orientation. In some embodiments, the present surgical system comprises a surgical retractor including radiolucent components configured to reduce scatter and/or other imaging interruptions caused by metallic components.

In some embodiments, the present surgical system comprises a surgical retractor including arms that can angulate up to about 25 degrees. In some embodiments, the present surgical system comprises a surgical retractor having a frictional fit joint connection mechanism for attaching components of the system. The friction fit joint is configured to maximize rigidity and minimize joint splay.

In some embodiments, the present surgical system comprises a retractor system having a minimized profile. In some embodiments, the present surgical system comprises a retractor having a rack that allows the arms to translate independently of each other. In some embodiments, the rack includes a length of about 200 mm to about 250 mm. In some embodiments, the rack is configured to connect to a table-mounted clamp.

In some embodiments, the present surgical system comprises a surgical retractor configured to minimize interference with bony anatomy. In some embodiments, the present surgical system comprises a surgical retractor configured to minimize interference with instruments during the surgical procedure. In some embodiments, the present surgical system comprises a surgical retractor configured to provide optimized lighting to working space. In some embodiments, the present surgical system comprises a surgical retractor configured to provide adequate purchase on tissue when fully retracted. In some embodiments, the present surgical system comprises a surgical retractor configured to accommodate varying patient sizes.

In some embodiments, the present surgical system comprises a surgical retractor configured to provide a force on tissue of about 60 pound-force. In some embodiments, the present surgical system comprises a surgical retractor including blades of various sizes from about 40 mm to about 110 mm. In some embodiments, the present surgical system comprises a surgical retractor configured to include radiolucent components while various components, such as, for example, latches, gears, threads may be machined from metal.

In some embodiments, the present surgical system comprises a surgical retractor blade including a surface that defines an opening in a front plane and/or a top plane of the blade to facilitate manipulation of one or more surgical instruments. In some embodiments, the surface openings in the front plane and/or the top plane of the blade allow the one or more surgical instruments to be angulated laterally and/or cephalad-caudally, while distal surface openings of the blade allow for anatomical relief, for example, along a midline lumbar fusion (MIDLF) surgical approach.

In some embodiments, the present surgical system comprises a surgical retractor blade including a surface that defines teeth disposed in an arcuate configuration and/or a rectangular cutout that provides anatomical relief and allows the blade to be disposed in the working surgical field and/or wound without impinging on the facets or the transverse processes. In some embodiments, the present surgical system comprises a surgical retractor blade including a surface that defines a large cutout in a front plane and/or a top plane of the blade to allow for instrumentation to be angulated up to approximately 30 degrees medial-laterally, as well as up to 20 degrees in the cephalad-caudal direction, respectively. In some embodiments, the surgical retractor blade facilitates a contra-lateral decompression and discectomy during a midline posterior transforaminal lumbar (TL) surgical approach, while decreasing surgical procedure duration.

In some embodiments, the present surgical system can be employed with a method for treating a spine including the step of connecting and/or slidably engaging one or more surgical retractor blades with a mating retraction rack. In some embodiments, the method includes the step of manipulating the retraction rack to laterally translate the blades. In some embodiments, the method includes the step of manipulating and/or drawing the blades into tension, thereby retracting an incision in the working surgical field.

In some embodiments, the present surgical system comprises a surgical retractor blade including a surface that defines an arc or cutout on a distal end thereof to provide anatomical relief, which allows the blade to be disposed in the working surgical field and/or wound at a selected depth. In some embodiments, this configuration allows surgical instrumentation to be angulated and disposed through the cutout, which opens a working space in the working surgical field and/or wound to facilitate the procedure, for example, a discectomy. In some embodiments, the present surgical system comprises a surgical retractor blade that can be manufactured via an additive manufacturing process, for example, 3D printing.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 includes a surgical instrument, such as, for example, a surgical retractor 12 having a pair of radiolucent retractor blades, such as, for example, blade 14 and blade 14a, similar to blade 14 described herein. Blade 14 is configured to provide selective orientation and positioning of a surgical instrument and/or support of patient anatomy. Blades 14, 14a are attached with a part, such as, for example, a gear rack 100 such that blades 14, 14a are independently movable in one or a plurality of degrees of freedom to one or a plurality of orientations relative to rack 100, stationary surgical equipment and/or a patient body B in connection with a surgical procedure.

Figure 2:
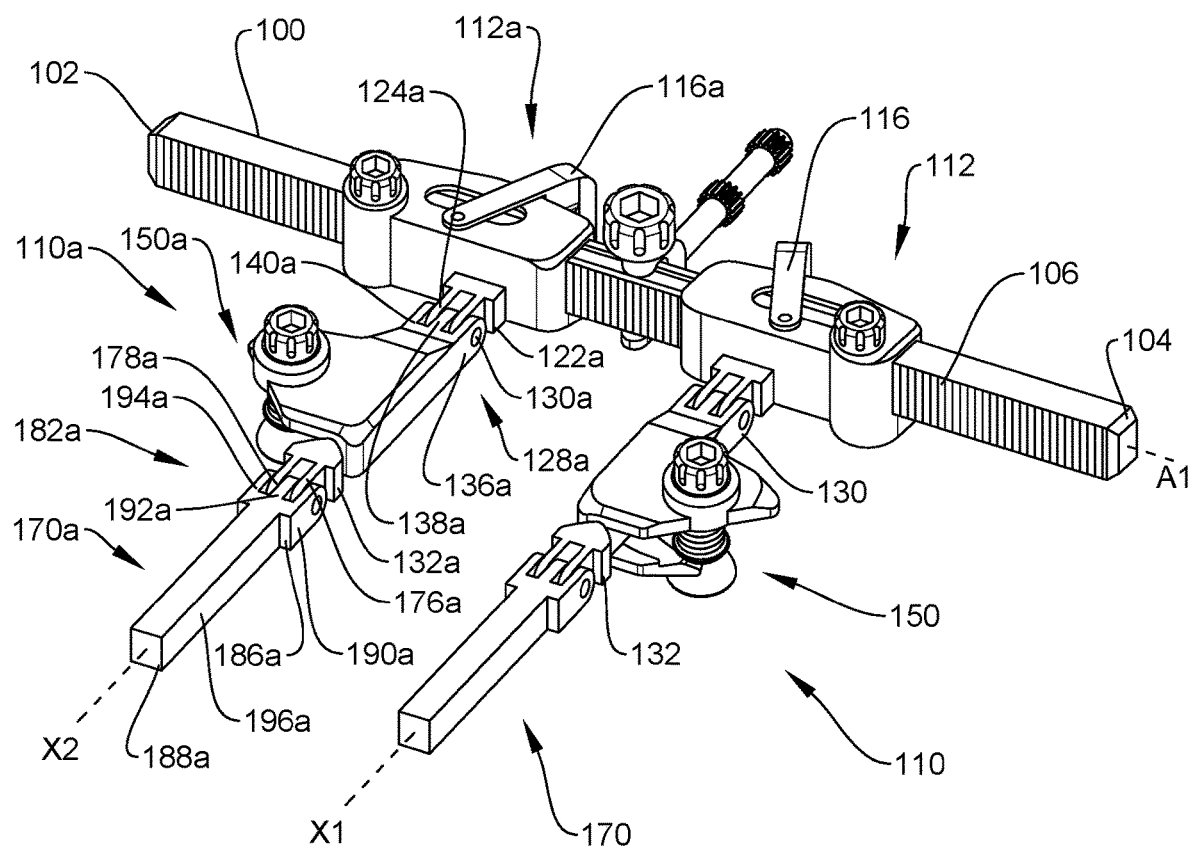
FIG. 2 is a perspective view of components of one embodiment of a surgical system in accordance with the principles of the present disclosure.

Rack 100 extends between an end 102 and an end 104 defining a longitudinal axis A1, as shown in FIG. 2. In some embodiments, rack 100 includes a length of about 200 mm to about 250 mm. Rack 100 is configured to connect adjacent blades 14, 14a to each other, as shown in FIG. 1. Rack 100 includes an outer surface having a plurality of teeth, such as, for example, splines 106. An extension 110 is engageable with rack 100 via a module 112. In some embodiments, rack 100 includes a radiolucent material.

Module 112 is configured for connection with rack 100. Module 112 includes an inner surface that includes a gear 114 engageable with rack 100 in a bi-directional and/or two-way ratchet configuration. The ratchet configuration is configured to resist and/or prevent movement of blade 14 relative to rack 100 in a first and/or a second direction. Module 112 includes a latch 116, which is engageable selectively with splines 106. In some embodiments latch 116 includes a pinion or pawl (not shown in detail) engageable with splines 106. In some embodiments, module 112 includes a radiolucent material.

Module 112 includes a surface 118 that includes flanges 120, 122 extending therefrom. Flanges 120, 122 extend perpendicular to surface 118 in a spaced apart orientation. In some embodiments, flanges 120, 122 may extend, for example, transverse or at angular orientations such as acute or obtuse, coaxial and/or may be offset or staggered relative to surface 118. Flange 120 includes a surface 124 and flange 122 includes a surface 126. Surfaces 124, 126 are configured to form a friction fit joint 128 with a portion of extension 110, as described herein. The friction fit between module 112 and extension 110 is configured to provide a rigid connection between extension 110 and module 112 and minimize splay at joint 128.

Figure 3:
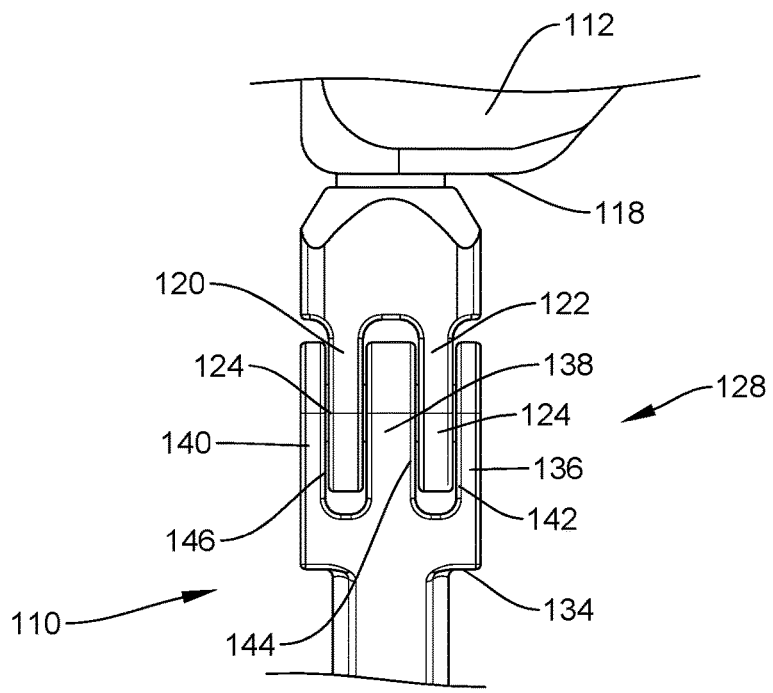
FIG. 3 is a top break-away view of the components shown in FIG. 2.
Figure 7:
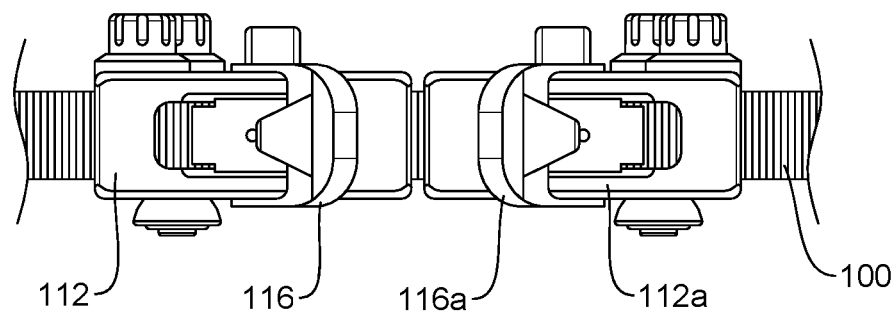
FIG. 7 is a side view of the components shown in FIG. 6.

Extension 110 extends between an end 130 and an end 132 defining an axis X1, as shown in FIG. 2. Extension 110 includes a surface 134 that includes flanges 136, 138, 140 extending therefrom, as shown in FIG. 3. Flanges 136, 138, 140 are configured for engagement with flanges 120, 122, as described herein. Flanges 136, 138, 140 extend perpendicular to surface 134 in a spaced apart orientation. In some embodiments, flanges 136, 138, 140 may extend, for example, transverse or at angular orientations such as acute or obtuse, coaxial and/or may be offset or staggered relative to surface 134. Flange 136 includes a surface 142, flange 138 includes a surface 144 and flange 140 includes a surface 146. Surfaces 142, 144, 146 are configured to form joint 128 with module 112, as described herein. The friction fit between module 112 and extension 110 is configured to provide a rigid connection between extension 110 and module 112 and minimize splay at joint 128.

Extension 110 includes a body 148 for housing a pivot joint 150 configured to selectively disposed blade 14 relative to blade 14a, rack 100, stationary surgical equipment and/or patient body B in connection with a surgical procedure. In some embodiments, body 148 includes a radiolucent material. Pivot joint 150 includes a spheroidal joint 152 including a spheroidal part 156 and a collar 158. Collar 158 is configured for relative movement along part 156. Pivot joint 150 includes a lock 160 releasably engageable with spheroidal joint 152 to fix blade 14 in the selected orientation. Lock 160 includes an actuator, for example, a screw 162 and a knob 164. Screw 162 includes a surface 166 configured for engagement with spheroidal joint 152 to resist and/or prevent movement of collar 158 relative to part 156, as shown in FIG. 5. In some embodiments, surface 166 includes a convex configuration. Knob 164 is actuated, for example, by rotation in a first direction to translate screw 162 into engagement with spheroidal joint 152. Knob 164 is actuated, for example, by rotation in a second direction to translate screw 162 out of engagement with spheroidal joint 152 to allow movement of extension 110. Extension 110 is pivotable about pivot joint 150 to allow blade 14 to rotate into a selected angle α1 relative to axis X1. In some embodiments, angle α1 is in a range of about 0 degrees to about 25 degrees.

Extension 110 is connectable with an arm 170, as shown in FIG. 4. Extension 110 includes a surface 172 that includes flanges 174, 176 extending therefrom. Flanges 174, 176 extend perpendicular to surface 172 in a spaced apart orientation. In some embodiments, flanges 174, 176 may extend, for example, transverse or at angular orientations such as acute or obtuse, coaxial and/or may be offset or staggered relative to surface 172. Flanges 174, 176 are configured to form a friction fit joint 182, similar to joint 128, with a portion of arm 170, as described herein. The friction fit between arm 170 and extension 110 is configured to provide a rigid connection between arm 170 and extension 110 and minimize splay at joint 182.

Arm 170 extends between an end 184 and an end 186, as shown in FIG. 4. In some embodiments, arm 170 includes a radiolucent material. Arm 170 includes a surface 188 that includes flanges 190, 192, 194, similar to flanges 142, 144, 146, as described herein. Flanges 190, 192, 194 are configured for engagement with flanges 176, 180, as described herein. Flanges 190, 192, 194 extend perpendicular to surface 134 in a spaced apart orientation. In some embodiments, flanges 190, 192, 194 may extend, for example, transverse or at angular orientations such as acute or obtuse, coaxial and/or may be offset or staggered relative to surface 134. Flange 190, 192, 194 are configured to form joint 182 with extension 110, as described herein. Arm 170 includes a jog 196 configured for connection with a portion of blade 14, as described herein.

An extension 110a, similar to extension 110 described herein, is engageable with rack 100 via a module 112a, similar to module 112 described herein, as described herein. Extensions 110, 110a are independently moveable relative to rack 100 via modules 112, 112a between ends 102, 104. In some embodiments, extension 110a includes a radiolucent material.

Module 112a is configured for connection with rack 100, as described herein. In some embodiments, module 112a includes a radiolucent material. Module 112a includes an inner surface that includes a gear 114a, similar to gear 114 described herein, engageable with rack 100 in a bi-directional and/or two-way ratchet configuration. The ratchet configuration is configured to resist and/or prevent movement of blade 14a relative to rack 100 in a first and/or a second direction. Module 112a includes a latch 116a, similar to latch 116 described herein, which is engageable selectively with splines 106. In some embodiments latch 116a includes a pinion or pawl (not shown in detail) engageable with splines 106.

Module 112a includes a surface 118a that includes flanges 120a, 122a, similar to flanges 120, 122 described herein, extending therefrom. Flanges 120a, 122a are configured to form a friction fit joint 128a with a portion of extension 110a, as described herein. The friction fit between module 112a and extension 110a is configured to provide a rigid connection between extension 110a and module 112a and minimize splay at joint 128a, as described herein.

Extension 110a extends between an end 130a and an end 132a defining an axis X2, as shown in FIG. 2. Extension 110a includes a surface 134a that includes flanges 136a, 138a, 140a, similar to flanges 136, 138, 140 described herein, extending therefrom, as shown in FIG. 2. Flanges 136a, 138a, 140a are configured for engagement with flanges 120a, 122a, as described herein, to form joint 128a with module 112a, as described herein.

Extension 110a includes a body 148a that houses a pivot joint 150a, similar to pivot joint 150 described herein, configured to selectively disposed blade 14a relative to blade 14, rack 100, stationary surgical equipment and/or patient body B in connection with a surgical procedure, as described herein. In some embodiments, body 148a includes a radiolucent material. Extension 110a is pivotable about pivot joint 150a to allow blade 14a to rotate into a selected angle α2 relative to axis X2. In some embodiments, angle α2 is in a range of about 0 degrees to about 25 degrees.

Extension 110a is connectable with an arm 170a, as described herein. In some embodiments, arm 170a includes a radiolucent material. Extension 110a includes a surface 172a that includes flanges 174a, 176a, similar to flanges 174, 176 described herein. Flanges 174a, 176a are configured to form a friction fit joint 182a, similar to joint 128, with a portion of arm 170a, as described herein.

Arm 170a extends between an end 184a and an end 186a, as shown in FIG. 2. Arm 170a includes flanges 190a, 192a, 194a, similar to flanges 190, 192, 194 described herein. Flanges 190a, 192a, 194a are configured for engagement with flanges 176a, 180a, as described herein, to form joint 182a with extension 110a, as described herein. Arm 170a includes a jog 196a configured for connection with a portion of blade 14a, as described herein.

Figure 8:
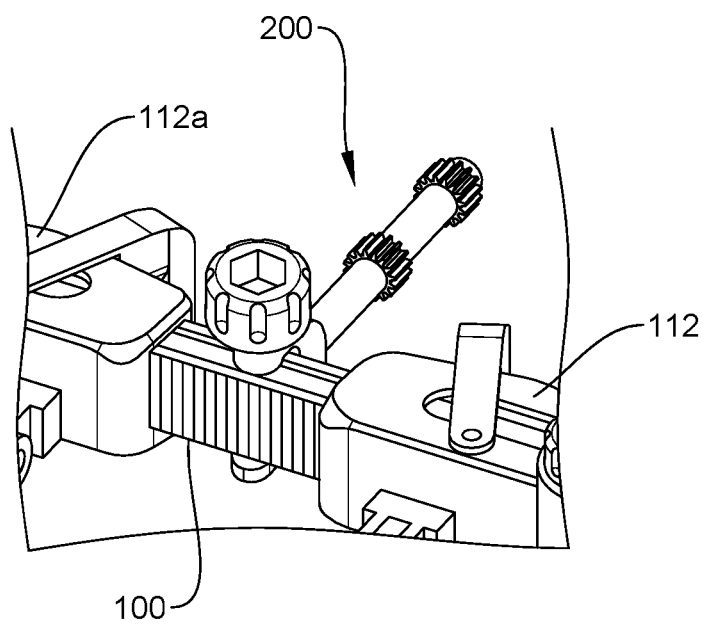
FIG. 8 is a break-away perspective view of components of one embodiment of a system in accordance with the principles of the present disclosure.

In some embodiments, rack 100 is engaged with a flex arm adaptor 200, as shown in FIG. 8, configured to connect surgical retractor 12 with a table mounted clamp (not shown). Portions of rack 100, extensions 110, 110a and/or arms 170, 170a are radiolucent, as described herein, allowing for an enhanced visualization of the surgical site by navigation components by reducing scatter and other imaging disruptions caused by metallic components. In some embodiments, portions of rack 100, extensions 110, 110a and/or arms 170, 170a are manufactured with carbon fiber. In some embodiments, portions of rack 100, extensions 110, 110a and/or arms 170, 170a, for example, latches, gears and/or threads are machined from metallic materials to maintain a strength and/or rigidity required for such components.

Blade 14 includes surfaces and/or openings to provide the selective orientation and positioning of the surgical instrument and/or support of the patient anatomy, as described herein. For example, blade 14 is configured to support and/or provide limitation of movement of a surgical instrument in a selected orientation relative to a surgical site, such as, for example, angulation of a surgical instrument in medial-lateral orientation and/or a cephalad-caudad orientation during a midline thoracolumbar approach. In some embodiments, surgical retractor 12 may include one or a plurality of blades 14. Blades 14, 14a are radiolucent allowing for an enhanced visualization of the surgical site by navigation components by reducing scatter and other imaging disruptions caused by metallic components. In some embodiments, blades 14, 14a are manufactured with carbon fiber. In some embodiments, blades 14, 14a include various lengths that range from about 40 mm to about 110 mm. In some embodiments, blades 14, 14a are configured to withstand a force of about 60 pound-force (lbf) to about 120 lbf of resistance from tissue, as shown by arrows C in FIG. 16, to facilitate retraction of tissue.

Figure 9:
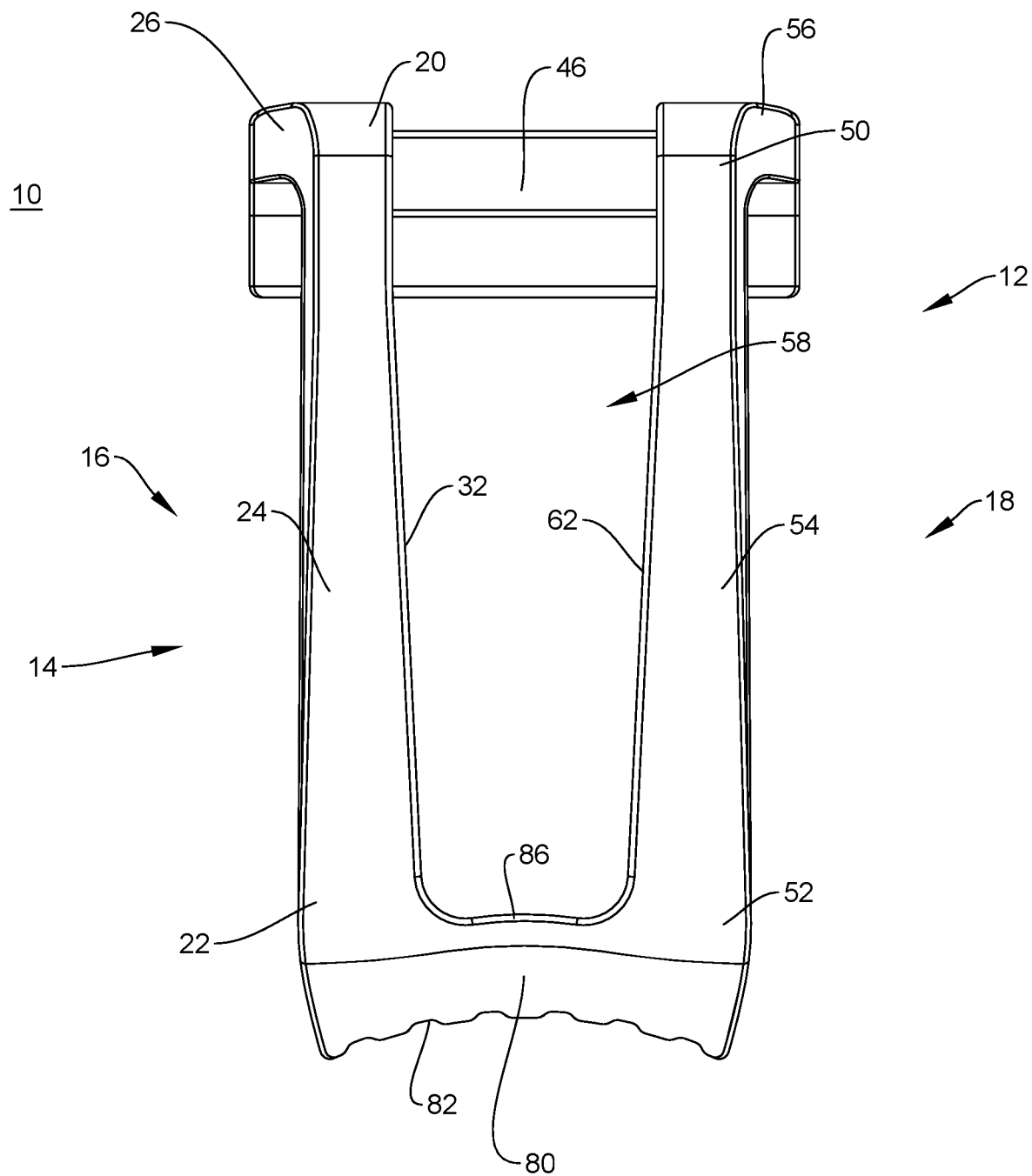
FIG. 9 is a side view of components of one embodiment of a surgical system in accordance with the principles of the present disclosure.

Blade 14 includes an arm 16 and an arm 18 being spaced apart from arm 16, as shown in FIG. 9. Arm 16 includes a portion 24 and a portion 26. Portion 24 extends between an end 20 and an end 22 along an axis X3 in a plane P1. In some embodiments, plane P1 is disposed a cephalad-caudad orientation relative to a patient body B. Portion 24 includes a surface 30 configured for engaging and spacing apart tissue. Portion 24 includes a surface 32 extending along axis X3 in plane P1. Surface 32 provides a limit to and/or restricts a range of movement of a surgical instrument to facilitate selective orientation and positioning of the surgical instrument within plane P1, as described herein.

Portion 26 extends along an axis X4 at an angular orientation, such as, for example, perpendicular to axis X2, as shown in FIG. 9. In some embodiments, portion 26 may be oriented in alternate configurations, such as, for example, parallel, co-axial, angularly offset, offset and/or staggered relative to portion 24. Portion 26 extends between an end 40 and an end 42 along axis X2 in a plane P2. In some embodiments, plane P2 is disposed in a medial-lateral orientation relative to patient body B. Portion 26 includes a surface 44 that provides a limit to and/or restricts a range of movement of a surgical instrument to facilitate selective orientation and positioning of the surgical instrument along plane P1.

Figure 10:
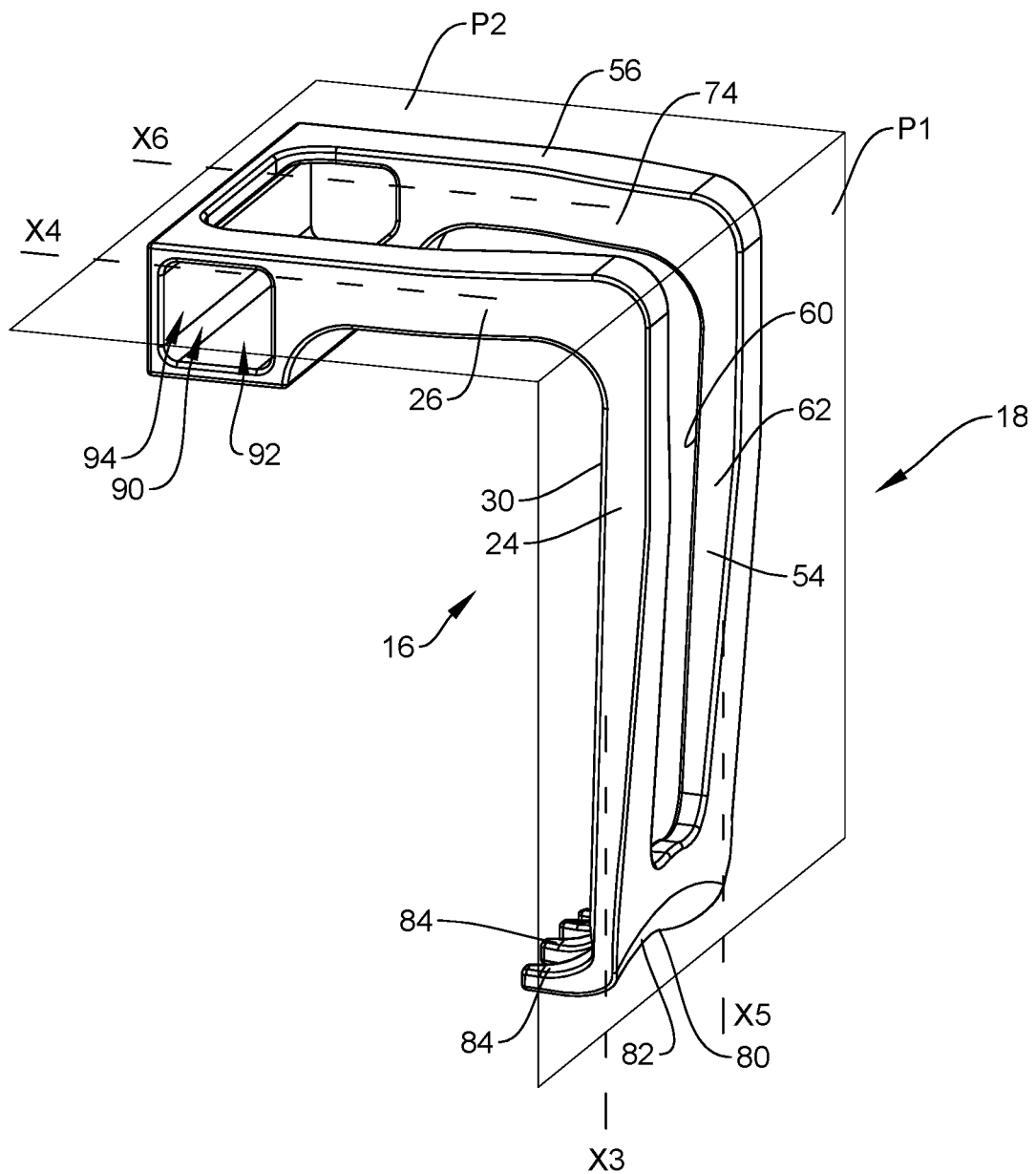
FIG. 10 is a perspective view of the components shown in FIG. 9.

Surface 46 extends between arms 16, 18 and is configured to position a surgical instrument in a selected orientation along plane P2. In some embodiments, surface 46 extends perpendicular to axes X4, X6, as shown in FIG. 10. In some embodiments, surface 46 may be oriented in alternate configurations, such as, for example, parallel, co-axial, angularly offset, offset and/or staggered relative to axes X4, X6.

In some embodiments, all or only a portion of arm 16 may have various cross-section configurations, such as, for example, arcuate, cylindrical, oblong, rectangular, polygonal, undulating, irregular, uniform, non-uniform, consistent, variable, and/or U-shape. In some embodiments, surface 32, surface 44 and/or surface 46 may have alternate surface configurations, such as, for example, rough, undulating, porous, semi-porous, dimpled, polished and/or textured.

Arm 18 includes a portion 54 and a portion 56. Portion 54 extends between an end 50 and an end 52 parallel to portion 24 along an axis X5 in plane P1. Portion 54 includes a surface 60 configured for engaging and spacing apart tissue. Portion 24 and portion 54 are spaced apart to form an opening 58 along plane P1 for disposal of a surgical instrument in a selected orientation along plane P1. Portion 54 includes a surface 62 that provides a limit to and/or restricts a range of movement of a surgical instrument to facilitate selective orientation and positioning of the surgical instrument along plane P1.

Figure 11:
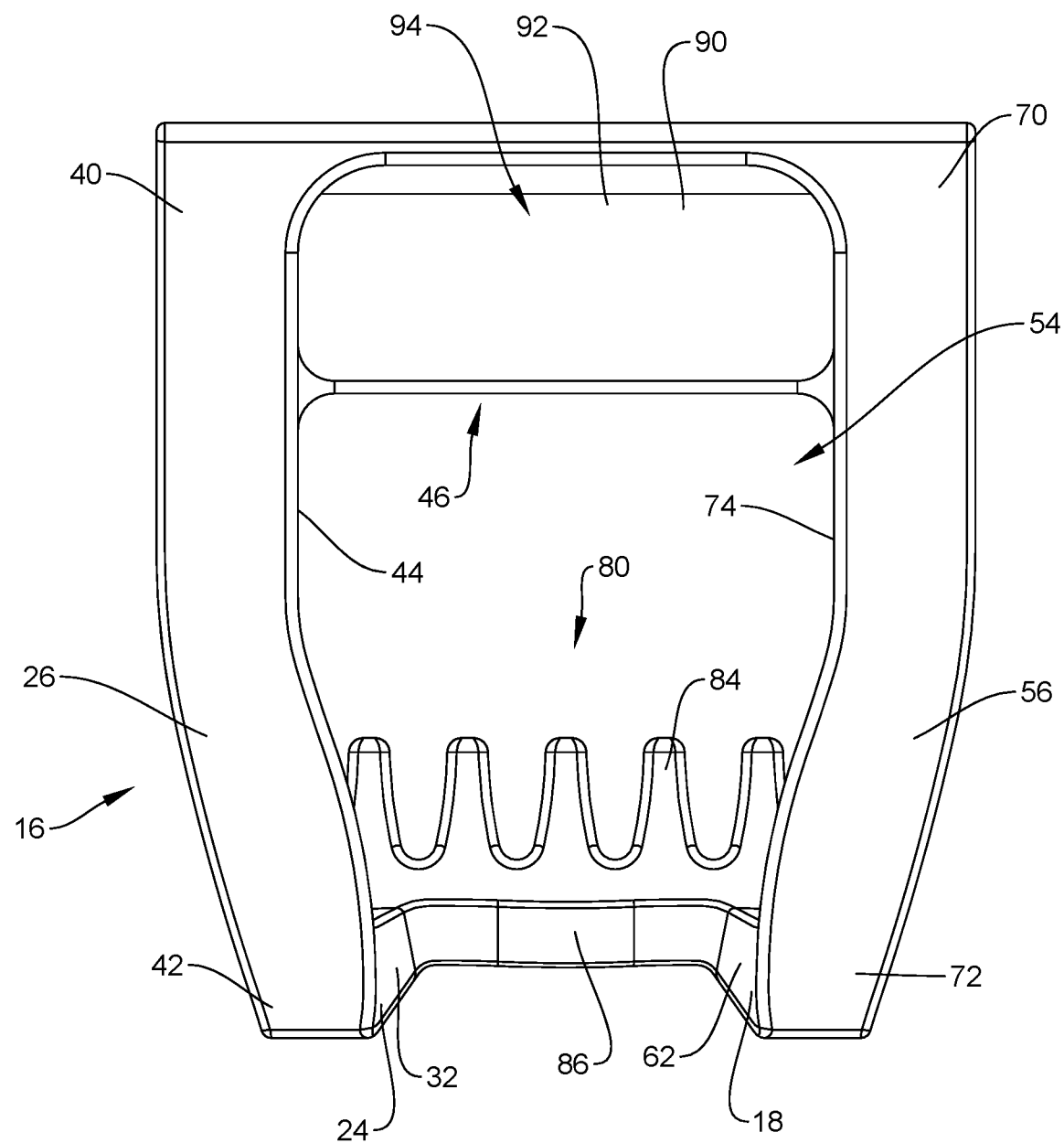
FIG. 11 is a top view of the components shown in FIG. 9.

Portion 56 extends along an axis X6, disposed parallel to axis X4, and at an angular orientation, such as, for example, perpendicular to axis X5, as shown in FIG. 10. In some embodiments, portion 56 may be oriented in alternate configurations, such as, for example, parallel, co-axial, angularly offset, offset and/or staggered relative to portion 54. Portion 56 extends between an end 70 and an end 72 along axis X6 in plane P2, as described herein. Portion 26 and portion 56 are spaced apart to form an opening 59 along plane P2 for disposal of a surgical instrument in a selected orientation along plane P1 and/or P2. Portion 56 includes a surface 74, as shown in FIG. 11, which provides a limit to and/or restricts a range of movement of a surgical instrument to facilitate selective orientation and positioning of the surgical instrument along plane P1. Openings 58, 59 are disposed in communication to facilitate movement of a surgical instrument along planes P1, P2.

In some embodiments, all or only a portion of arm 18 may have various cross-section configurations, such as, for example, arcuate, cylindrical, oblong, rectangular, polygonal, undulating, irregular, uniform, non-uniform, consistent, variable, and/or U-shape. In some embodiments, surface 62 and/or surface 76 may have alternate surface configurations, such as, for example, rough, undulating, porous, semi-porous, dimpled, polished and/or textured.

Blade 14 includes a member 80. Member 80 is connected with ends 22, 52 of arms 16, 18. Member 80 is disposed with arms 16, 18 to support, position, provide a limit and/or restrict a range of movement of a surgical instrument in a selected orientation relative to the surgical site. Member 80 includes a surface 82 having an arcuate configuration. Surface 82 is curved in a convex configuration between ends 22, 52 such that surface 82 provides for anatomical relief of body tissue. In some embodiments, surface 82 facilitates an increase of insertion of retractor 12 into patient body B adjacent to a working surgical field. In some embodiments, surface 82 is configured for insertion with a patient body B without impinging on the facets or the transverse processes. Surface 82 includes a plurality of teeth 84 extending transverse to surface 82, as shown in FIG. 10. Teeth 84 are configured to facilitate capture and/or separation of tissue. Member 80 includes a surface 86 disposed adjacent to surfaces 32, 62 to support, provide a limit and/or restrict a range of movement of a surgical instrument in a selected orientation relative to the surgical site.

Surfaces 32, 44, 62, 74 and/or 86 provide a limit to and/or restrict a range of movement of a surgical instrument to facilitate selective orientation and positioning of the surgical instrument, for example, along a cephalad-caudal direction relative to vertebral tissue within openings 58, 59 along plane P1. For example, the working end of a surgical instrument is engaged with and fixed with vertebral tissue. In some embodiments, the handle end of the surgical instrument is moveable through an angular range of 0 through 60 degrees relative to vertebral tissue along plane P1. In some embodiments, a surgical instrument is moveable through an angular range of 0 through 20 degrees relative to vertebral tissue along plane P1. Contact of a surgical instrument with surfaces 32, 44, 62, 74 and/or 86 provide limits on the range of movement and/or rotation of the surgical instrument through the angular range in plane P1.

Surfaces 46 and/or 86 provide a limit to and/or restrict a range of movement of a surgical instrument to facilitate selective orientation and positioning of the surgical instrument along, for example, a medial-lateral direction relative to the vertebral tissue within openings 58, 59 along plane P2. For example, the working end of the surgical instrument is engaged with and is fixed with vertebral tissue. In some embodiments, the handle end of the surgical instrument is moveable through an angular range of 0 through 40 degrees relative to vertebral tissue within plane P2. In some embodiments, the surgical instrument is moveable through an angular range of 0 through 30 degrees relative to vertebral tissue within plane P2. Contact of a surgical instrument with surfaces 46, 86 provide limits on the range of movement and/or rotation of the surgical instrument through the angular range in plane P2.

Ends 40, 70 include a mating portion 90 that extends along surface 46. Portion 90 includes a surface 92 that defines an opening 94. Opening 94 is configured for disposal of jogs 196 of retraction rack 100, as shown in FIG. 1.

Figure 12:
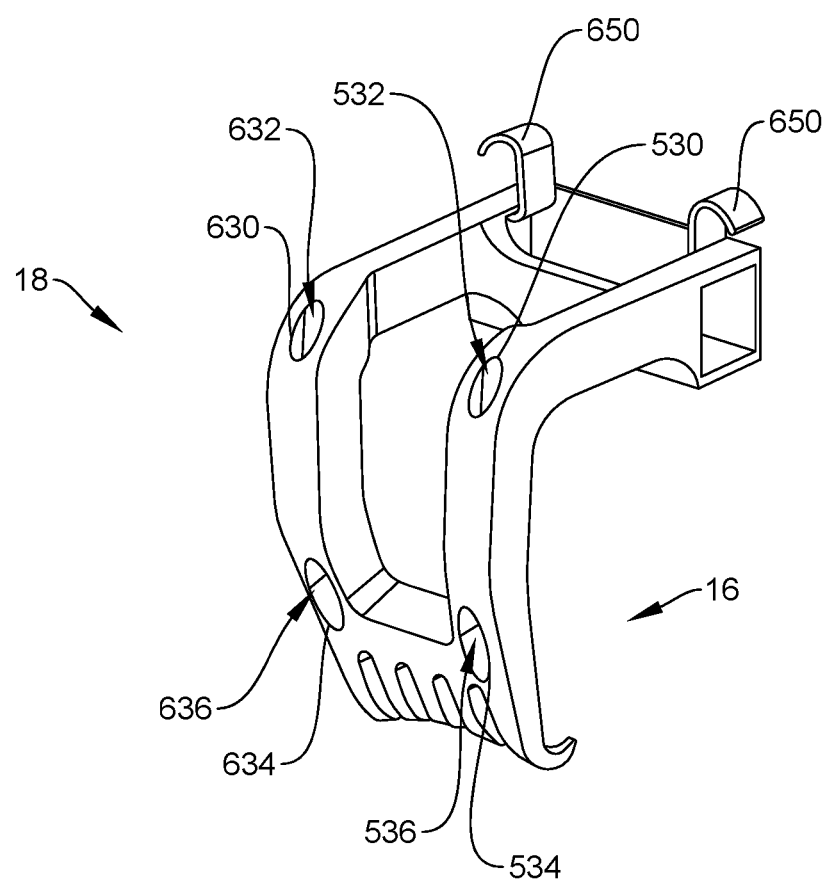
FIG. 12 is a perspective view of components of one embodiment of a system in accordance with the principles of the present disclosure.
Figure 13:
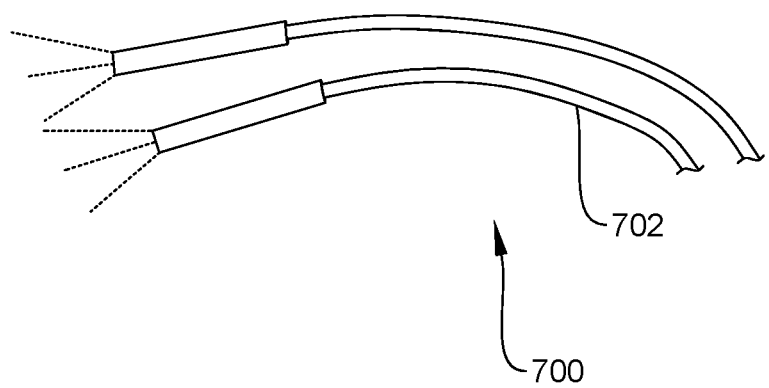
FIG. 13 is a perspective view of components of one embodiment of a system in accordance with the principles of the present disclosure.

In some embodiments, as shown in FIG. 12, Arm 16 includes a surface 530 that defines an opening 532 and an opening 534. A channel 536 extends between openings 532, 534. Channel 536 is configured for disposal of a light source 700, as shown in FIG. 13. Light source 700 is guided through channel 536 to provide light to the working space at the surgical site.

Arm 18 includes a surface 630 that defines an opening 632 and an opening 634. A channel 536 extends between openings 632, 634. Channel 536 is configured for disposal of light source 700, as described herein.

Portion 26 and portion 56 each include a flange, such as, for example, a hook 650, as shown in FIG. 12. Hooks 650 are configured to facilitate organization of extensions and/or cables 702 extending from light source 700. In some embodiments, hooks 650 are configured to resist and/or prevent cables 702 from obstructing visualization the surgical site and/or the ability to operate in the working space.

Blade 14 is attached with rack 100 for relative translation to space apart tissue. In some embodiments, a ratchet mechanism on rack 100 is configured to facilitate retraction of tissue. Blade 14 is attached with a rack 100 such that blade 14 is movable in one or a plurality of degrees of freedom to one or a plurality of orientations relative to rack 100, stationary surgical equipment and/or the patient body B in connection with a surgical procedure. In some embodiments, the degrees of freedom of movement of blade 14 to one or a plurality of orientations relative to rack 100, stationary surgical equipment and/or patient body B can include one or a plurality of degrees of movement in translation, one or a plurality of degrees of movement in rotation, planar movement such as a four bar linkage, spherical movement such as poly-axial and/or joints or links such as a kinematic chain. In some embodiments, the degrees of movement in translation can include up, down, left, right, forward and/or backward. In some embodiments, the degrees of movement in rotation can include tilting, swiveling and/or pivoting in one or a plurality of directions. In some embodiments, blade 14 is independently and selectively movable relative to rack 100, stationary surgical equipment and/or patient body B. In some embodiments, one or a plurality of blades 14 may be attachable with rack 100.

In some embodiments, retractor 12 may be employed with various surgical instruments, such as, for example, drivers, extenders, reducers, spreaders, distractors, clamps, forceps, elevators and drills, which may be alternately sized and dimensioned, and arranged as a kit. In some embodiments, surgical system 10 may comprise the use of microsurgical and image guided technologies, such as, for example, surgical navigation components employing emitters and sensors, which may be employed to track introduction and/or delivery of the components of surgical system 10 including the surgical instruments to a surgical site. See, for example, the surgical navigation components and their use as described in U.S. Pat. Nos. 6,021,343, 6,725,080, 6,796,988, the entire contents of each of these references being incorporated by reference herein.

In assembly, operation and use, surgical system 10, similar to the systems and methods described herein, is employed with a surgical procedure for treatment of a spinal disorder, such as those described herein, affecting a section of a spine of a patient. Surgical system 10 may also be employed with other surgical procedures. In some embodiments, surgical system 10 is employed to implant components, such as bone fasteners, rods, interbody devices and plates, with patient body B.

With the body disposed in a selected orientation, for example, for a midline posterior TL surgical approach for a contra-lateral decompression and discectomy, a medical practitioner makes and/or creates an incision in tissue, which includes soft tissue and/or muscle, to obtain access to a surgical site including affected vertebral levels of vertebrae V. The tissue is manipulated to space the tissue adjacent to the incision.

Surgical retractor 12, as described herein, is disposed with the incision for spacing tissue. Modules 112, 112a are connected with rack 100. Flanges 120, 122 are connected with flanges 136, 138, 140 to form fiction fit joint 128, as described herein. Flanges 120a, 122a and connected with flanges 136a, 138a, 140a to form fiction fit joint 128a, as described herein. Flanges 176, 180 are connected with flanges 190, 192, 194 to form joint 182, as described herein. Flanges 176a, 180a are connected with flanges 190a, 192a, 194a to form joint 182a, as described herein.

Blades 14, 14a, as described herein, are connected with jogs 196, 196a. Blades 14, 14a are relatively moveable and configured for insertion sequentially around the intervertebral space via pivot joints 150, 150a, as described herein.

Surfaces 280, 280a are positioned to provide anatomical relief and allow blades 14, 14a to be disposed in the working surgical field without impinging on the facets or the transverse processes, as described herein. Blades 14, 14a are manipulated for movement by rack 100, as described herein, relative to vertebrae.

Figure 16:
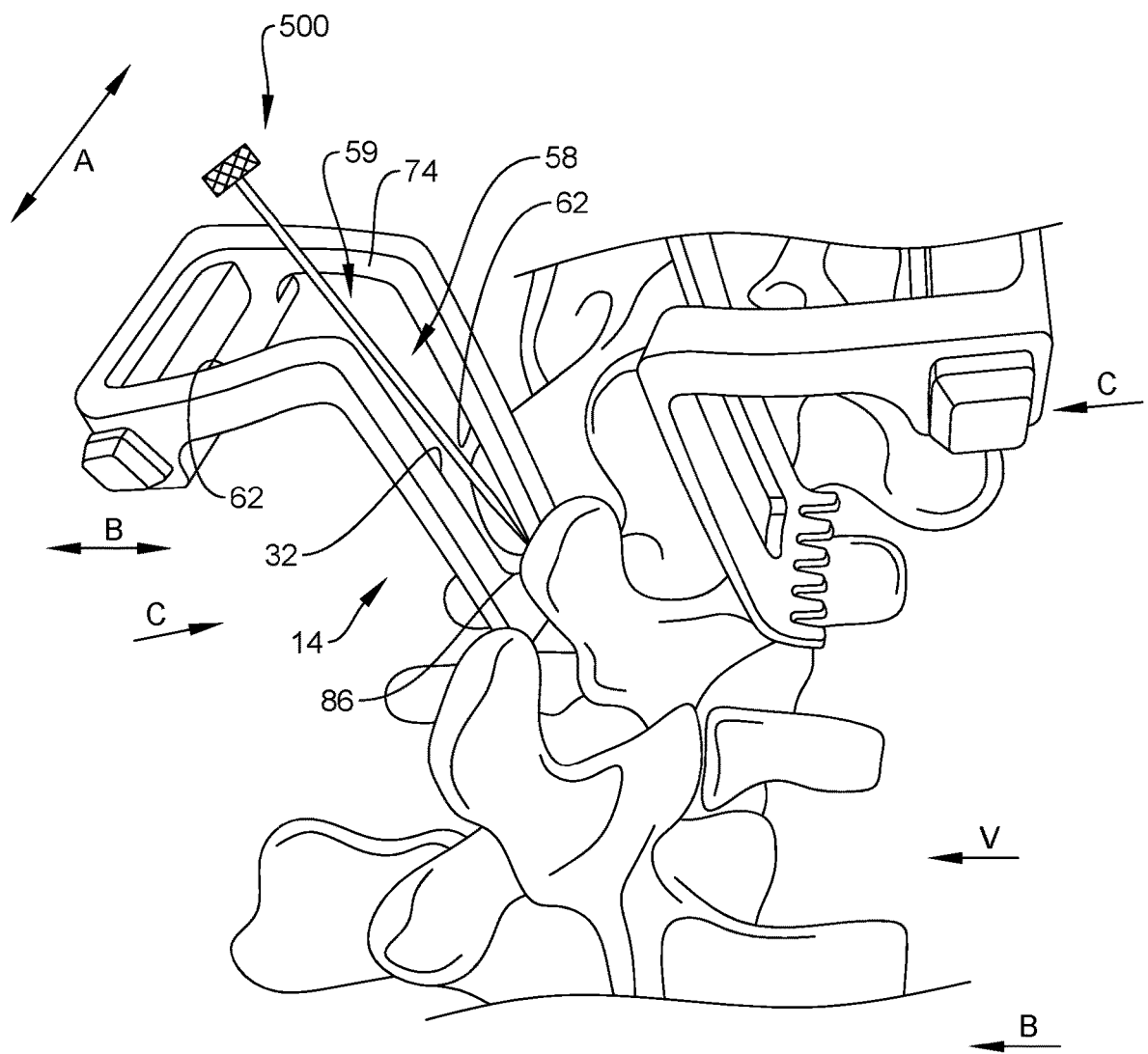
FIG. 16 is a perspective view of components of one embodiment of a system in accordance with the principles of the present disclosure disposed with a patient body.

Opening 59 is oriented in plane P2 that is disposed in the cephalad-caudal direction of vertebrae V and opening 58 is oriented in plane P1 disposed in a medial-lateral direction relative to vertebrae. A surgical instrument 500 is inserted through opening 59 and opening 58, as shown in FIG. 16.

Figure 14:
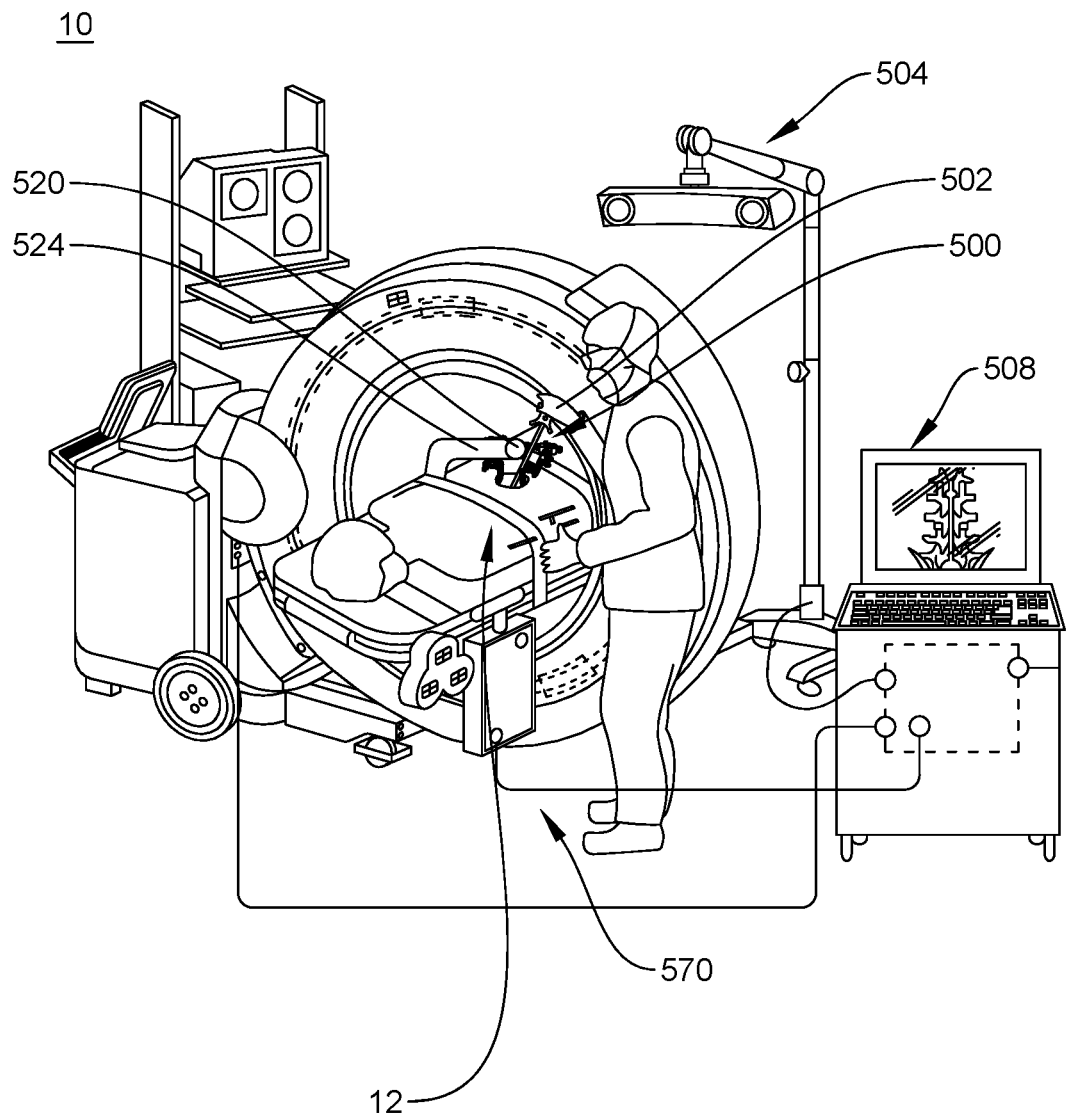
FIG. 14 is a perspective view of components of one embodiment of a system in accordance with the principles of the present disclosure disposed with a patient body.
Figure 15:
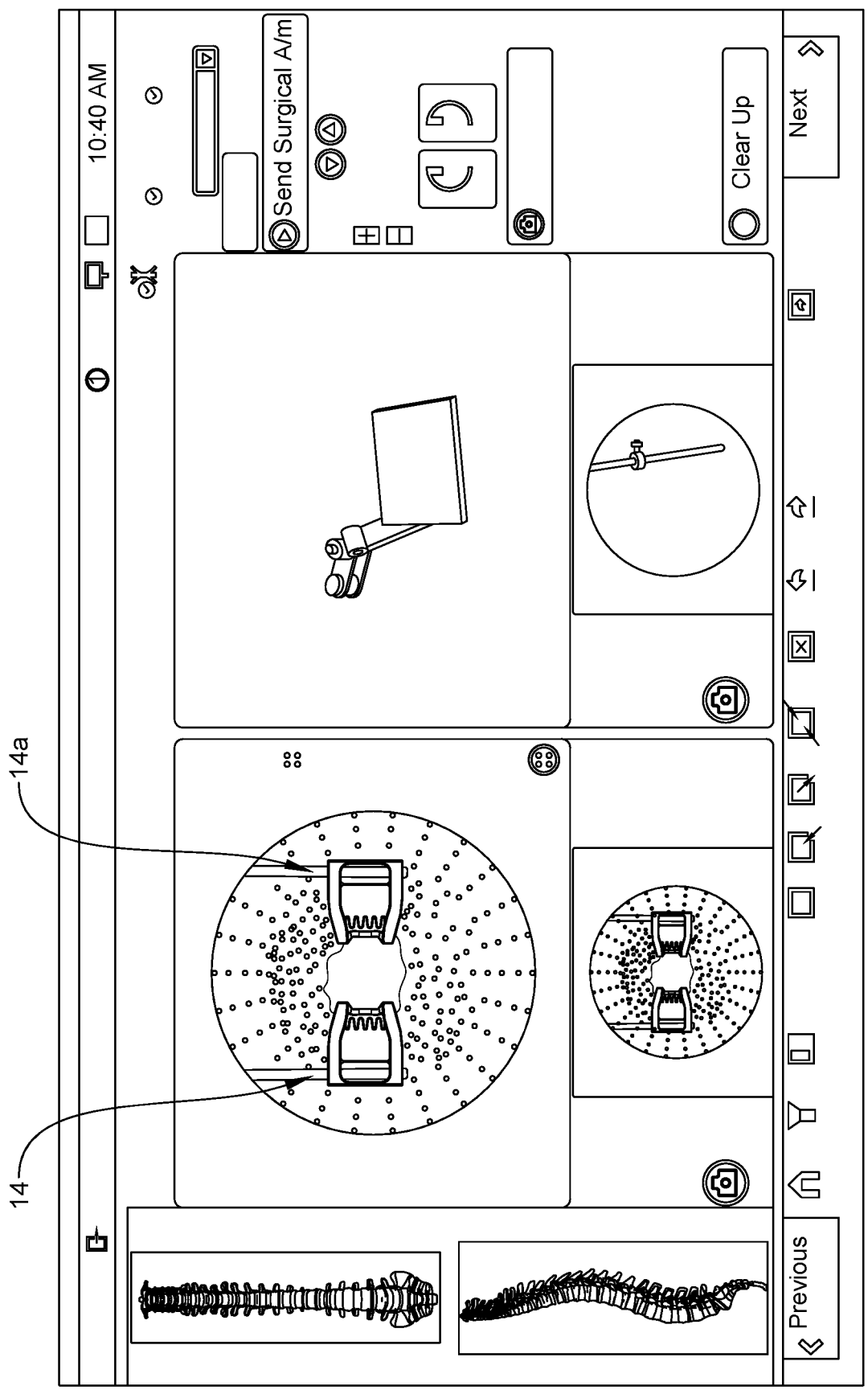
FIG. 15 is a graphical representation of a computer showing components of one embodiment of a spinal implant system in accordance with the principles of the present disclosure.

In some embodiments, surgical instrument 500 includes a navigation component 502, as shown in FIG. 14. Surgical instrument 500 is configured for disposal adjacent the surgical site such that the navigation component is oriented relative to a sensor array 504, as shown in FIG. 14, to facilitate communication between navigation component 502 and sensor array 504 during the surgical procedure, as described herein. Navigation component 502 is configured to generate a signal representative of a position of surgical instrument 500 relative tissue. The components of surgical system 10 including the radiolucent material remains relatively invisible on the images provided and grid elements can be located through blades 14, 14a, as shown in FIG. 15.

In some embodiments, sensor array 502 receives signals from to provide a three-dimensional spatial position and/or a trajectory of surgical instrument 500 relative to tissue. Data is generated for display of an image on a monitor 508. In some embodiments, sensor array 504 receives signals to provide a visual representation of a position of surgical instrument 500 relative to tissue. See, for example, similar surgical navigation components and their use as described in U.S. Pat. Nos. 6,021,343, 6,725,080, 6,796,988, the entire contents of each of these references being incorporated by reference herein.

The surgical navigation system is configured for acquiring and displaying medical imaging, for example, x-ray images appropriate for a given surgical procedure. In some embodiments, pre-acquired images of a patient are collected. In some embodiments, the surgical navigation system can include medical imaging, for example, an O-arm® imaging device 68 sold by Medtronic Navigation, Inc. having a place of business in Louisville, Colo., USA.

The surgical navigation system a tracking system 510, such as, for example, an optical tracking system that includes an optical localizer, such as, for example, sensor array 504 and/or an EM tracking system that can include an EM localizer. In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

In some embodiments, surgical instrument 500 is configured for use with end effector 520. End effector 520 includes a channel configured for passage of the components of surgical instrument 500, and/or spinal construct components, as described herein. A robotic arm 524 includes position sensors (not shown), similar to those referenced herein, which measure, sample, capture and/or identify positional data points of end effector 520 in three-dimensional space for a guide-wireless insertion of components of surgical instrument 500 and spinal constructs with selected vertebral levels. In some embodiments, a sleeve, which comprises an axial trajectory guide, is connected with robotic arm 524. In some embodiments, the position sensors of robotic arm 524 are employed in connection with the surgical navigation system to measure, sample, capture and/or identify positional data points of end effector 520 in connection with surgical treatment, as described herein. The position sensors are mounted with robotic arm 524 and calibrated to measure positional data points of end effector 520 in three-dimensional space, which are communicated to the components of a surgical robotic guidance system. See, for example, the surgical robotic guidance systems and methods described in U.S. Pat. No. 8,571,638, the contents of which being hereby incorporated by reference herein in its entirety.

For example, the surgical navigation system registers the patient anatomy relative to the location of the robot, which includes the location of the robot's end effector 520, such that robotic arm 524 extends and moves relative to a base of the robot to assist in surgical procedures. The patient anatomy and the robot may each have reference markers, which are visible by the surgical navigation system. This, in combination with imaging of the patient anatomy, as described herein and stored with the surgical robotic guidance system and/or the surgical navigation system, enables registering the patient's anatomy with respect to location of the robot. The components of surgical system 10 including the radiolucent material remains relatively invisible on the images provided during registration. Grid elements can be located through blades 14, 14a.

As surgical instrument 500 is manipulated, contact with surfaces 32, 44, 62, 74 and/or 86 provide a limit to and/or restrict a range of movement of a surgical instrument, as described herein, to facilitate selective orientation and positioning of surgical instrument 500 in the cephalad-caudal direction, as shown by arrows A in FIG. 16, within opening 59 and opening 58.

As surgical instrument 500 is manipulated, contact with surfaces 46 and/or 86 provide a limit to and/or restrict a range of movement of surgical instrument 500 in the medial-lateral direction within opening 59 and opening 58, as shown by arrows B in FIG. 16. Surgical instrument 500 is moveable through an angular range of 0 through 30 degrees relative to vertebrae V along the medial-lateral direction of vertebrae V. Surgical instrument 500 is moveable through an angular range of 0 through 20 degrees relative vertebrae V along the cephalad-caudal direction of vertebrae V.

Surgical instrument 500 and an image guide are oriented relative to a sensor to communicate a signal representative of a position of blades 14, 14*a*. A tracking device is provided and includes a sensor that receives the signal and communicates with a processor to generate data for display of an image from a monitor, the image representing position of blades 14, 14*a* relative to tissue. In some embodiments, an end effector of a robotic arm is positioned with blades 14, 14*a* to direct surgical instrument 500 into the surgical site.

In some embodiments, pilot holes or the like are made in vertebrae V adjacent the intervertebral space for receiving bone fasteners and/or attaching spinal constructs, which may include rods and plates. An inserter is attached with the implants and/or spinal constructs for delivery adjacent to a surgical site for implantation adjacent one or more vertebra and/or intervertebral spaces of the vertebral levels.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiopaque markers may be included for identification under x-ray, fluoroscopy, CT or other imaging techniques. In some embodiments, the use of surgical navigation, microsurgical and image guided technologies, as described herein, may be employed to access, view and repair spinal deterioration or damage, with the aid of surgical system 10. In some embodiments, surgical system 10 may include implants and/or spinal constructs, which may include one or a plurality of plates, rods, connectors and/or bone fasteners for use with a single vertebral level or a plurality of vertebral levels.

It will be understood that various modifications and/or combinations may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical retractor comprising:
a part extending parallel to a longitudinal axis along an entire length of the part;
a first radiolucent blade connected with the part;
a second radiolucent blade connected with the part, the first and second blades being independently translatable relative to the part; and
at least one of the first and second blades including spaced apart arms, the arms being connected via a member, the member and the arms being configured to guide at least one surgical instrument in a selected orientation relative to a surgical site,
wherein the first extension is rotatable relative to the part about a first pivot axis extending parallel to the longitudinal axis, the second extension being rotatable relative to the part about a second pivot axis extending parallel to the longitudinal axis.

2. A surgical retractor as recited in claim 1, further comprising first and second extensions coupled to the part, the arms of the first blade including a first portion connected with the first extension and a second portion engageable with tissue to define a first opening adjacent a spine, the arms of the second blade including a third portion connected with the second extension and a further portion engageable with tissue to define a second opening adjacent a spine.

3. A surgical retractor as recited in claim 2, wherein the second extension extends parallel to the first extension.

4. A surgical retractor as recited in claim 2, wherein the first portion defines a first plane and the second portion defines a second plane disposed at a perpendicular orientation relative to the first plane, the third portion defining a third plane and the fourth portion defining a fourth plane disposed at a perpendicular orientation relative to the third plane.

5. A surgical retractor as recited in claim 2, wherein the first extension is offset relative to the first opening adjacent the spine, the second extension being offset relative to the second opening adjacent the spine.

6. A surgical retractor as recited in claim 1, wherein the part includes a gear rack.

7. A surgical retractor as recited in claim 1, further comprising a ratchet coupled to the part, the ratchet being configured for preventing movement of at least one of the first and second blades relative to the part in a first direction and a second direction.

8. A surgical retractor as recited in claim 1, further comprising at least one lock coupled to the part to selectively dispose the first blade relative to the second blade.

9. A surgical retractor as recited in claim 1, wherein a mating surface of the arms of the first blade comprises a first channel, the arms of the second blade defining a second channel, the first extension being disposed in the first channel, the second extension being disposed in the second channel.

10. A surgical retractor as recited in claim 1, wherein the first extension and the first blade are rotatable about the first pivot axis in an angular range from 0 degrees to 25 degrees, the second extension and the second blade being rotatable about the second pivot axis in an angular range from 0 degrees to 25 degrees, the first and second pivot axes each extending parallel to the longitudinal axis.

11. A surgical retractor as recited in claim 1, wherein the first extension includes a first section coupled to the part and a second section, the first blade being coupled to the second section, the first section being rotatable relative to the part about the first pivot axis, the second section being rotatable relative to the first section about the second pivot axis, the second extension including a third section coupled to the part and a fourth section, the second blade being coupled to the third section, the third section being rotatable relative to the part about a third pivot axis, the fourth section being rotatable relative to the third section about a fourth pivot axis, the first pivot axis, the second pivot axis, the third pivot axis and the fourth pivot axis each extending parallel to the longitudinal axis.

12. A surgical retractor as recited in claim 1, wherein at least one of the first and second blades includes carbon fiber.

13. A surgical retractor as recited in claim 1, wherein at least a portion of the part includes carbon fiber.

14. A surgical retractor as recited in claim 1, wherein the part includes opposite first and second surfaces, the first surface including a plurality of splines, the first and second surfaces each extending parallel to the longitudinal axis along the entire length of the part.

15. A surgical retractor comprising:
a rack extending parallel to a longitudinal axis along an entire length of the rack;
a first extension;
a second extension, the extensions being independently movable relative to the rack;
a first radiolucent blade connected with and rotatable relative to the first extension; and
a second radiolucent blade connected with and rotatable relative to the second extension, the first and second blades being independently translatable relative to the rack,
each of the first and second blades including spaced apart arms being connected via a member, the member and the arms being configured to guide at least one surgical instrument in a selected orientation relative to a surgical site,
wherein the first extension is rotatable relative to the rack about a first pivot axis extending parallel to the longitudinal axis, the second extension being rotatable relative to the rack about a second pivot axis extending parallel to the longitudinal axis.

16. A surgical retractor as recited in claim 15, wherein the arms of the first blade include a first portion connected with the first extension and a second angled portion engageable with tissue to define an opening adjacent a spine, and the arms of the second blade include a first portion connected with the second extension and a second angled portion engageable with tissue to define the opening.

17. A surgical retractor as recited in claim 16, wherein the extensions are independently translatable relative to the rack and are connected to the first portions of the first and second arms such that the extensions are disposable in an offset orientation relative to the opening.

18. A surgical retractor comprising:
a rack extending along a longitudinal axis between opposite first and second ends, the rack comprising opposite first and second surfaces each extending continuously from the first end to the second end, the first surface including a plurality of splines, the first and second surfaces each extending parallel to the longitudinal axis along the entire length of the rack;
a first housing comprising a first channel and a first bracket, the first end being positioned in the first channel;
a second housing comprising a second channel and a second bracket, the second end being positioned in the second channel;
a first extension comprising a first section coupled to the first bracket and a second section, the first section being pivotable relative to the first bracket about a first pivot axis, the second section being pivotable relative to the first section about a second pivot axis;
a second extension comprising a third section coupled to the second bracket and a fourth section, the third section being pivotable relative to the second bracket about a third pivot axis, the fourth section being pivotable relative to the third section about a fourth pivot axis, the first pivot axis, the second pivot axis, the third pivot axis and the fourth pivot axis each extending parallel to the longitudinal axis, the first and second extensions being independently movable relative to the rack;
a first radiolucent blade comprising a third channel, the second section being positioned in the third channel to couple the first radiolucent blade to the first housing; and
a second radiolucent blade comprising a fourth channel, the fourth section being positioned in the fourth channel to couple the second radiolucent blade to the second housing,
where the first and second radiolucent blades each include spaced apart arms connected via a member, the member and the arms being relatively disposed in a configuration to guide at least one surgical instrument in a selected orientation relative to a surgical site.

19. A surgical retractor as recited in claim 18, wherein the first extension and the second extension each extend perpendicular to the longitudinal axis.

* * * * *